United States Patent
Bindayel

(10) Patent No.: US 10,159,541 B2
(45) Date of Patent: Dec. 25, 2018

(54) ORTHODONTIC SYSTEMS

(71) Applicant: Naif Bindayel, Riyadh (SA)

(72) Inventor: Naif Bindayel, Riyadh (SA)

(*) Notice: Subject to any disclaimer, the term of this patent is extended or adjusted under 35 U.S.C. 154(b) by 0 days.

(21) Appl. No.: 15/160,291

(22) Filed: May 20, 2016

(65) Prior Publication Data
US 2017/0128167 A1 May 11, 2017

Related U.S. Application Data

(60) Provisional application No. 62/252,760, filed on Nov. 9, 2015.

(51) Int. Cl.
| | | |
|---|---|---|
| A61C 7/14 | (2006.01) | |
| A61B 90/98 | (2016.01) | |
| A61C 7/20 | (2006.01) | |
| A61C 7/00 | (2006.01) | |
| A61C 7/12 | (2006.01) | |
| A61C 7/22 | (2006.01) | |
| A61C 7/28 | (2006.01) | |
| A61B 5/00 | (2006.01) | |
| A61B 90/00 | (2016.01) | |

(52) U.S. Cl.
CPC ............ *A61B 90/98* (2016.02); *A61B 5/4547* (2013.01); *A61B 5/6802* (2013.01); *A61C 7/002* (2013.01); *A61C 7/12* (2013.01); *A61C 7/14* (2013.01); *A61C 7/20* (2013.01); *A61C 7/22* (2013.01); *A61C 7/28* (2013.01); *A61B 5/0022* (2013.01); *A61B 2090/064* (2016.02); *A61B 2560/0219* (2013.01); *A61B 2560/045* (2013.01); *A61B 2562/0252* (2013.01)

(58) Field of Classification Search
CPC .. A61C 7/285; A61C 7/12; A61C 7/14; A61C 7/22; A61C 7/141; A61C 7/143; A61C 7/145; A61C 7/148; A61C 7/16; A61C 7/18; A61C 7/287; A61C 1/003; A61C 1/04; A61C 1/06; A61B 90/98; A61B 2090/064; A61B 2560/045
See application file for complete search history.

(56) References Cited

U.S. PATENT DOCUMENTS

| | | | | |
|---|---|---|---|---|
| 4,243,387 A | * | 1/1981 | Prins ........................ | A61C 7/12 433/16 |
| 4,292,025 A | | 9/1981 | Förster | |

(Continued)

FOREIGN PATENT DOCUMENTS

WO    WO 03/096922    11/2003

OTHER PUBLICATIONS

Final Office Action for U.S. Appl. No. 15/160,255 dated Aug. 29, 2017.

(Continued)

*Primary Examiner* — Heidi M Eide
(74) *Attorney, Agent, or Firm* — Fish & Richardson P.C.

(57) ABSTRACT

An orthodontic system includes an orthodontic bracket that has a base configured to be attached to a surface of a tooth. The bracket includes a rotatable module having a first member and a second member, the rotatable module being rotatably coupled to the base, the first and second members being spaced apart to define an archwire slot configured to receive an archwire. The base includes a miniature gear system to drive the rotatable module relative to the base.

66 Claims, 11 Drawing Sheets

(56) References Cited

U.S. PATENT DOCUMENTS

| | | | |
|---|---|---|---|
| 5,032,080 | A | 7/1991 | Hakansson et al. |
| 5,035,614 | A | 7/1991 | Greenfield |
| 5,876,206 | A * | 3/1999 | Maurer .................. A61C 17/34 15/22.1 |
| 5,954,502 | A | 9/1999 | Tuenge et al. |
| 6,632,088 | B2 | 10/2003 | Voudouris |
| 7,306,458 | B1 | 12/2007 | Lu |
| 7,581,714 | B2 | 9/2009 | Machu |
| 9,531,237 | B2 | 12/2016 | Miller |
| 2001/0029008 | A1 | 10/2001 | Jordan et al. |
| 2003/0031975 | A1 | 2/2003 | Voudouris |
| 2003/0152889 | A1 * | 8/2003 | Uji ..................... A61C 13/0024 433/169 |
| 2005/0026102 | A1 | 2/2005 | Miller |
| 2005/0269821 | A1 * | 12/2005 | Nadel ..................... F03B 13/20 290/1 R |
| 2006/0074431 | A1 * | 4/2006 | Sutton .................. A61B 17/025 606/90 |
| 2007/0184399 | A1 | 8/2007 | Salich |
| 2008/0248439 | A1 | 10/2008 | Griffith et al. |
| 2009/0286195 | A1 * | 11/2009 | Sears ....................... A61C 7/14 433/8 |
| 2009/0317757 | A1 * | 12/2009 | Lemchen ................. A61C 7/14 433/24 |
| 2012/0148973 | A1 | 6/2012 | Johnston |
| 2014/0134562 | A1 | 5/2014 | Wu et al. |
| 2014/0272751 | A1 * | 9/2014 | Cosse ..................... A61C 7/02 433/9 |
| 2015/0305833 | A1 * | 10/2015 | Cosse .................... A61C 7/002 433/3 |

OTHER PUBLICATIONS

International Search Report and Written Opinion of the International Searching Authority for International Application No. PCT/IB2016/056759 dated Apr. 4, 2017.

Non-Final Office Action for U.S. Appl. No. 15/160,234 dated Apr. 10, 2017.

Non-Final Office Action for U.S. Appl. No. 15/160,255 dated Apr. 5, 2017.

Non-Final Office Action for U.S. Appl. No. 15/160,337 dated May 23, 2018.

Non-Final Office Action for U.S. Appl. No. 15/160,277 dated Jul. 18, 2018.

* cited by examiner

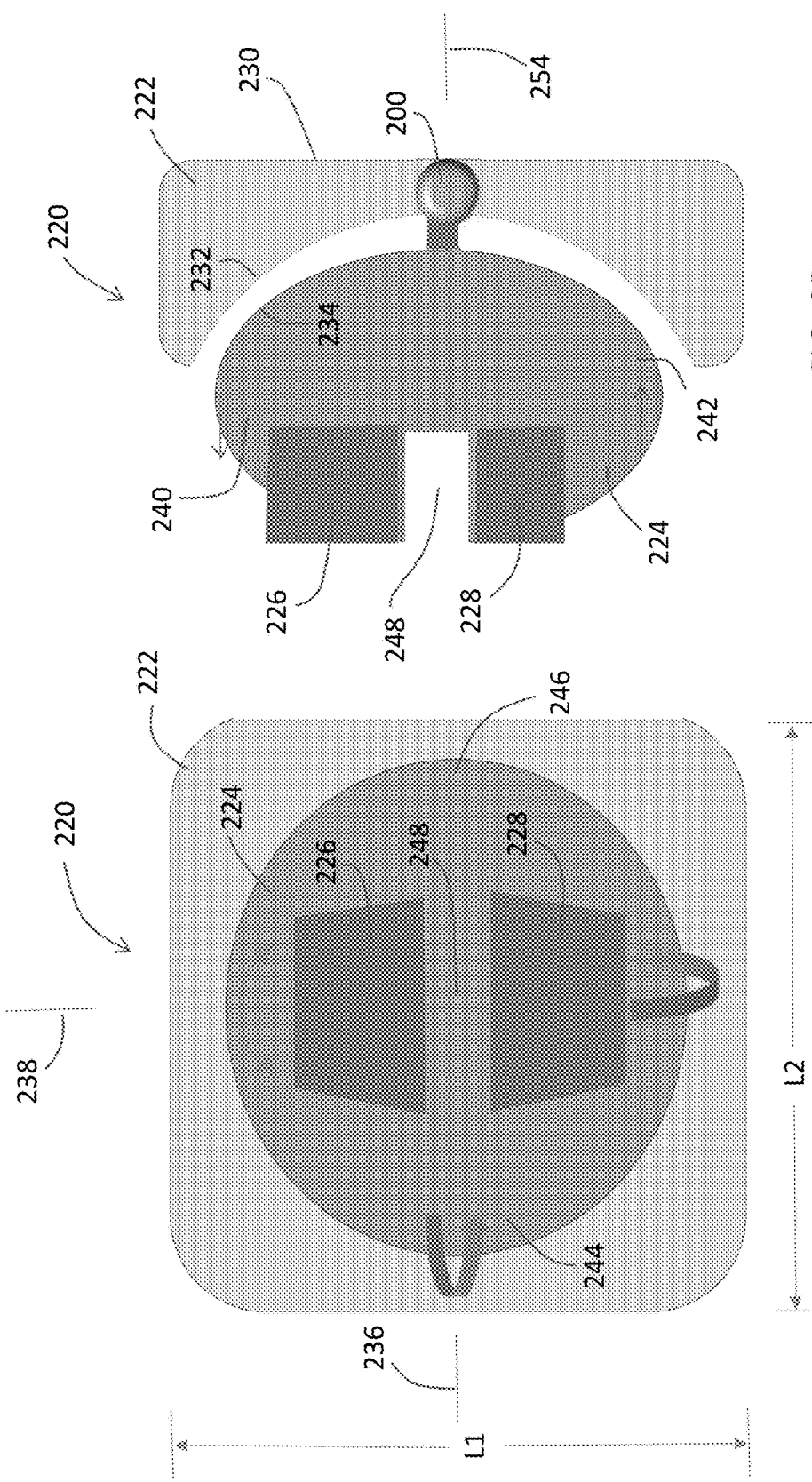

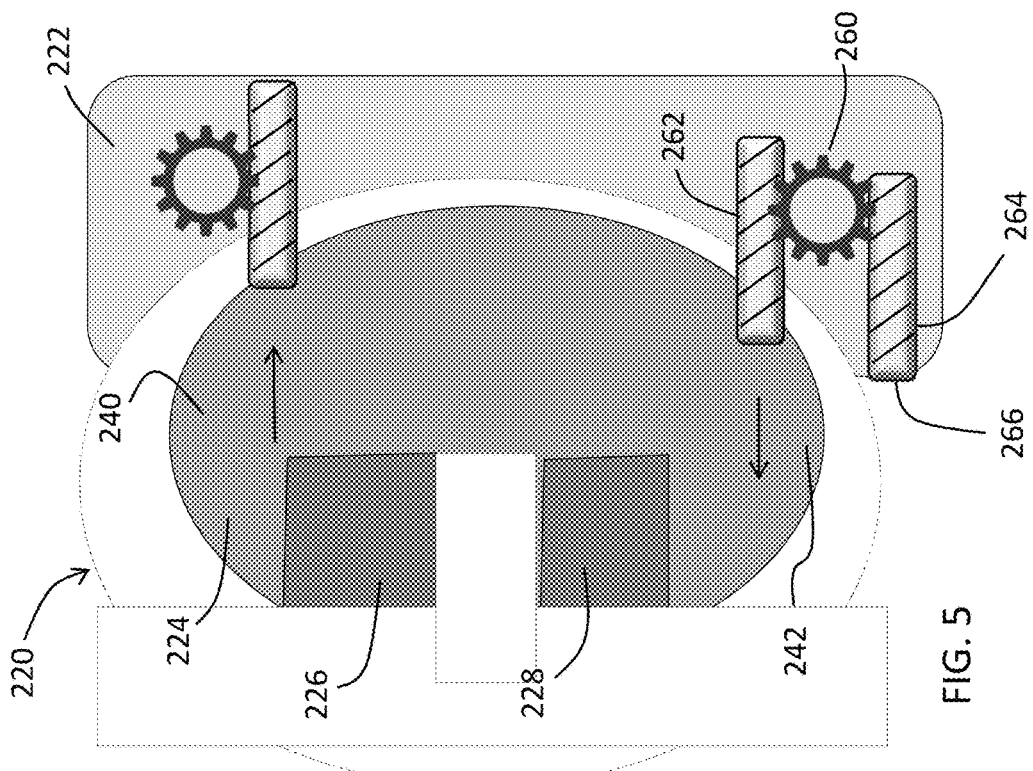
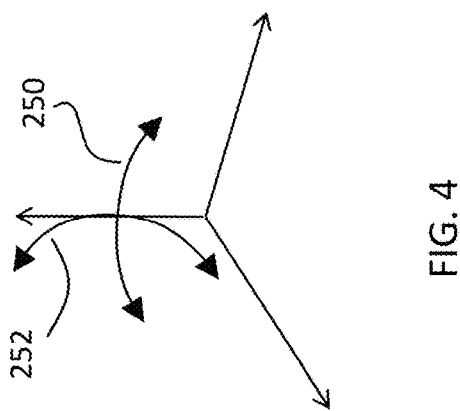
FIG. 5
FIG. 4

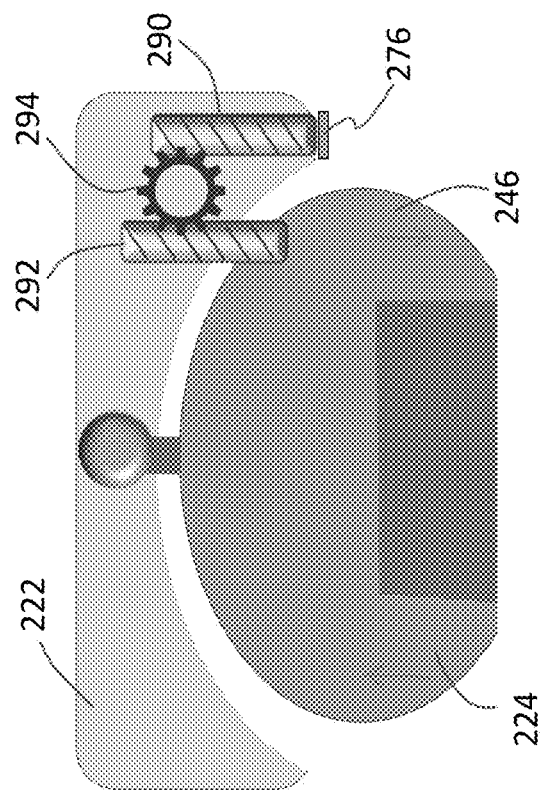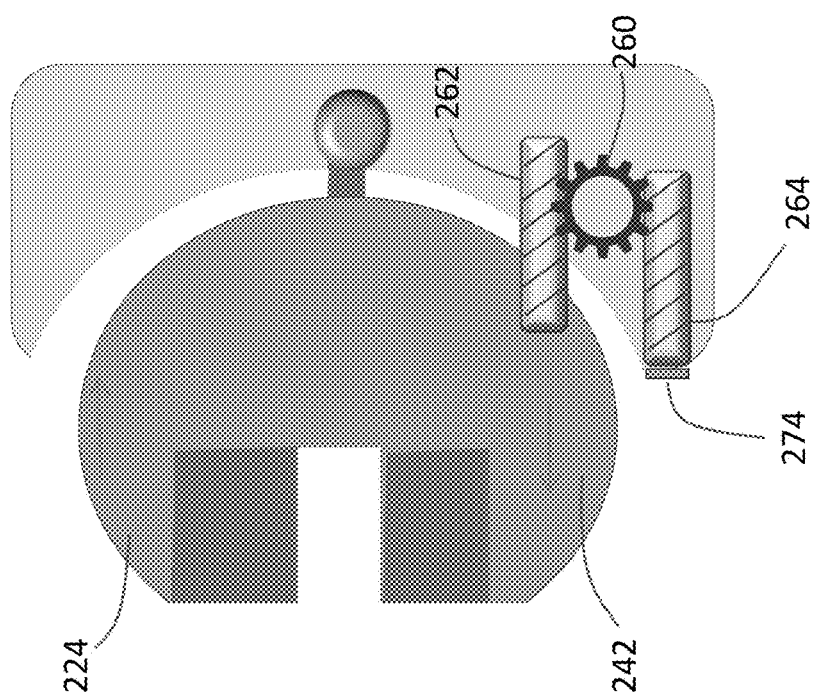
FIG. 6C
FIG. 6B

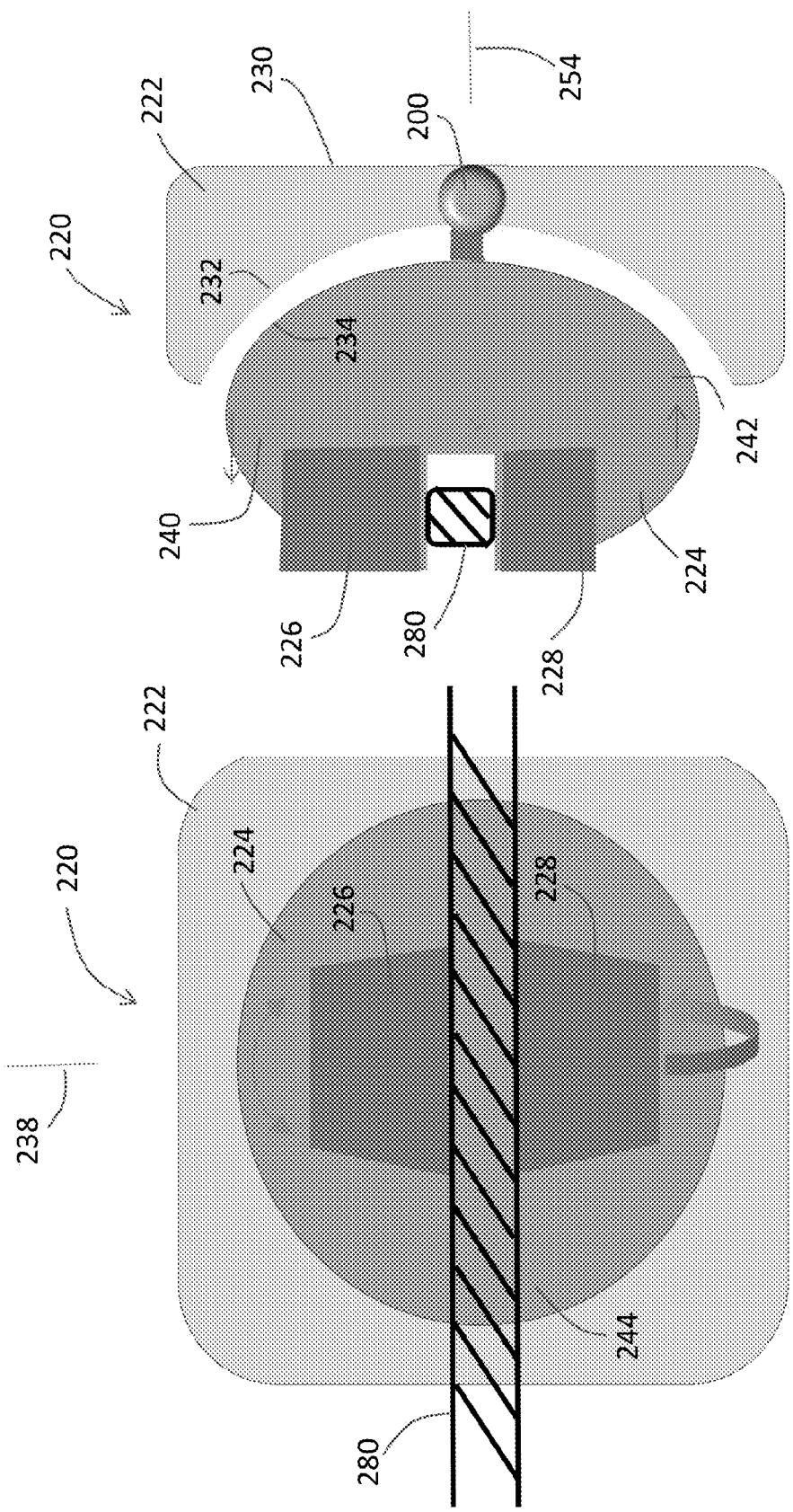

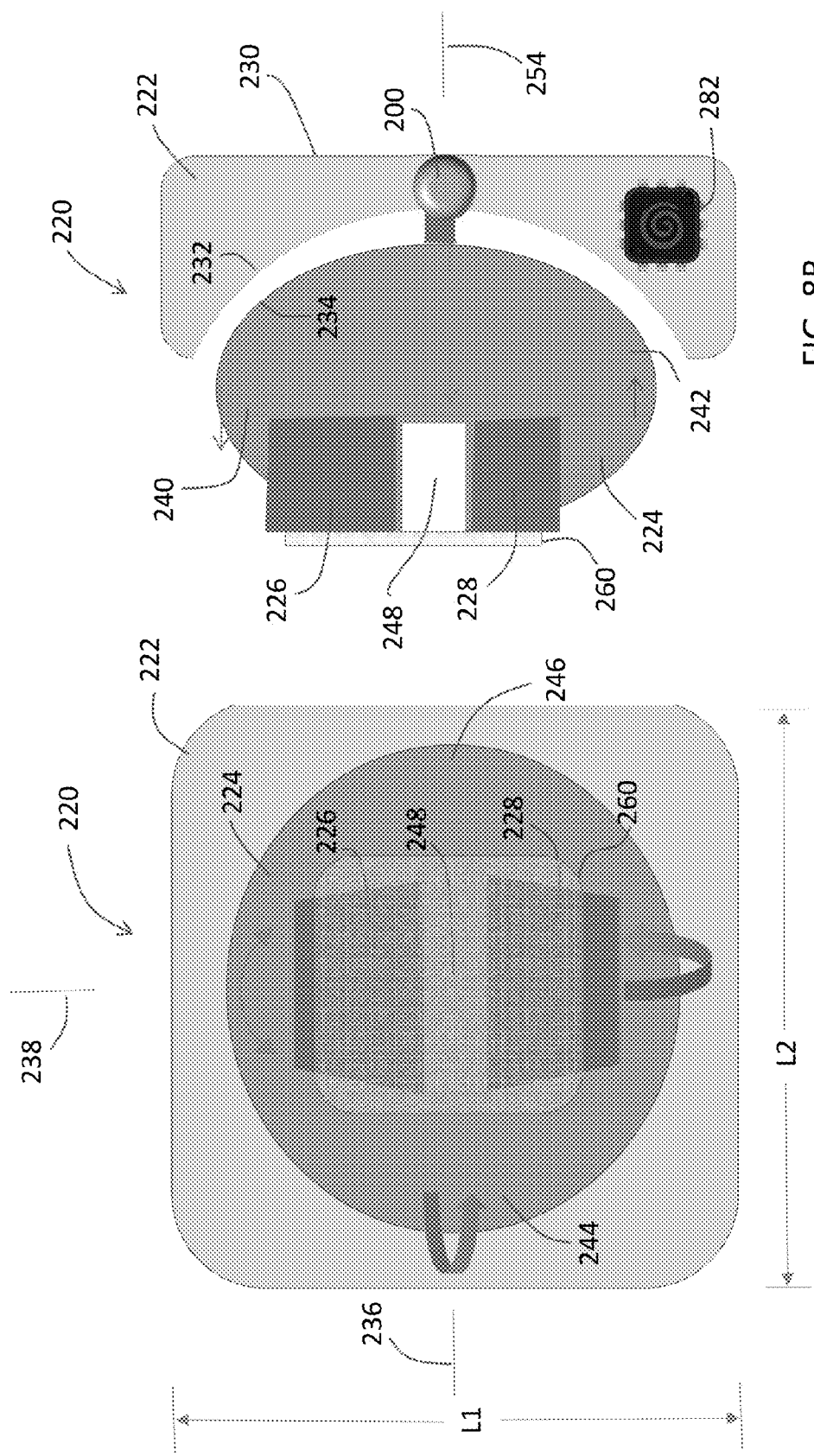

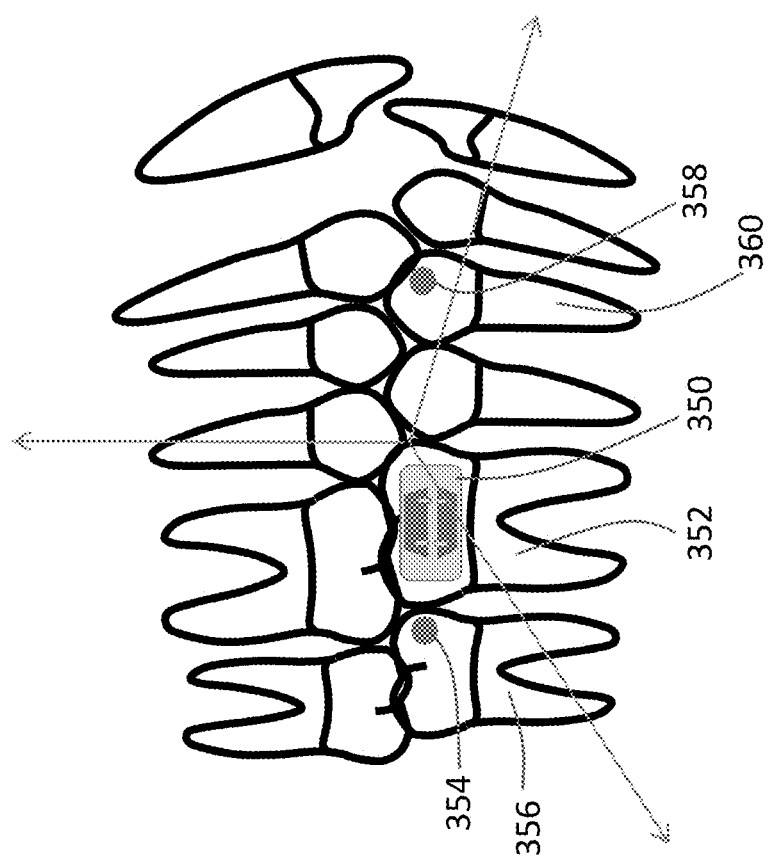

ORTHODONTIC SYSTEMS

CROSS-REFERENCE TO RELATED APPLICATIONS

This application claims priority to U.S. Provisional Patent Application 62/252,760, filed on Nov. 9, 2015. This application is related to U.S. patent applications 15/160,275, filed on May 20, 2016, 15/160,234, filed on May 20, 2016, 15/160,277, filed on May 20, 2016, 15/160,255, filed on May 20, 2016, and 15/160,337, filed on May 20, 2016. The contents of the above applications are incorporated by reference in their entirety.

TECHNICAL FIELD

This disclosure relates to orthodontic systems.

BACKGROUND

Orthodontic braces are useful in correcting alignment of teeth to proper positions and orientations in the dental arch and to improve dental health. In some examples, orthodontic braces include metal brackets bonded to the teeth and arch wires that are tied to the brackets by elastic ties. The arch wires are designed to apply force to the brackets and teeth, causing the teeth to slowly move or rotate in prescribed directions. The arch wires are adjusted, e.g., every three or four weeks during treatment to maintain pressure in order to supply prescribed forces to the teeth. There are many types of dental braces. For example, braces can be self-ligating such that the arch wire clips into the brackets without the need for ligatures. Some dental braces use computer-adjusted wires. These braces use the same principle of force delivery by an external source outside of the bracket (e.g., wire, coils, or elastics). In some examples, a bracket may have a base that is angulated to combine torque, angulation, in and out bend, and offsets for each tooth. This enables an unadjusted arch wire to perform variant alignment functions (i.e., with no further wire bending). In some examples, a series of clear molds may be used to produce teeth alignment. Orthodontic treatments generally last for two to three years.

SUMMARY

In a general aspect, an orthodontic bracket includes a base configured to be attached to a surface of a tooth; and a rotatable module having a first member and a second member, in which the rotatable module is rotatably coupled to the base, and the first and second members are spaced apart to define an archwire slot configured to receive an archwire. The base includes a miniature gear system to drive the rotatable module relative to the base.

In another general aspect, a method includes attaching a base of an orthodontic bracket to a surface of a tooth, in which the orthodontic bracket has a base and a rotatable module rotatably coupled to the base, the rotatable module has a first member and a second member, and the first and second members are spaced apart to define an archwire slot. The method includes inserting an archwire into the archwire slot; rotating the rotatable module relative to the base; generating a force based on an interaction of the archwire and walls of the archwire slot; and transmitting the force to the tooth.

In another general aspect, an orthodontic bracket includes a base configured to be attached to a surface of a tooth; and a rotatable module having an occlusal member and a gingival member, in which the rotatable module is rotatably coupled to the base, the occlusal member and the gingival member are spaced apart to define an archwire slot between the occlusal member and the gingival member, and the archwire slot is configured to receive an archwire. The base includes a miniature gear system to drive the rotatable module relative to the base.

In another general aspect, a method includes attaching a base of an orthodontic bracket to a surface of a tooth, in which the orthodontic bracket has a base and a rotatable module rotatably coupled to the base, the rotatable module has an occlusal member and a gingival member, and the occlusal member and the gingival member are spaced apart to define an archwire slot between a gingival surface of the occlusal member and an occlusal surface of the gingival member. The method includes inserting an archwire into the archwire slot; rotating the rotatable module relative to the base; generating a force based on an interaction of the archwire and walls of the archwire slot; and transmitting the force to the tooth.

Other aspects include other combinations of the features recited above and other features, expressed as methods, apparatus, systems, program products, and in other ways. Advantages of the aspects and implementations may include one or more of the following. The orthodontic brackets can be active brackets or smart brackets. A remote orthodontic system can allow active brackets or smart brackets to be remotely controlled or adjusted. The active brackets can generate force, and the force applied to the teeth can be increased or decreased while the patient is at home. The progress of teeth alignment can be monitored remotely. The remote orthodontic system can provide feedback and report symptoms, if any, to the orthodontist. In cases where adjustments to the original treatment plans are needed, the force adjustments can be made and applied while the patient is at home without the need to visit the dental clinic. The system can also provide an estimate of the remaining treatment time based on current progress of treatment. The system can reduce the trial and error in orthodontic treatment by using proper biomechanical pre-planning and insistent re-adjustment and monitoring. The system can improve the accessibility for orthodontic treatment in rural areas, and may reduce the number of days that school children miss classes. The orthodontic treatment outcomes may be more predictable, leading to a better quality with potentially reduced treatment side effects.

DESCRIPTION OF DRAWINGS

FIGS. 3A and 3B are diagrams of an exemplary e-Bracket.

FIG. 4 is a diagram of movement directions of the e-Bracket.

FIG. 5 is a vertical cross sectional view of the e-Bracket along a direction orthogonal to the longitudinal direction of the orthodontic wire.

FIGS. 6B and 6C are cross-sectional diagrams of the e-Bracket of FIG. 6A.

FIGS. 7A, 7B, 8A, and 8B are diagrams of an exemplary e-Brackets.

FIG. 10 is a diagram of a smart bracket and exemplary reference markers.

Like reference symbols in the various drawings indicate like elements.

DETAILED DESCRIPTION

This document describes an orthodontic system that enables an orthodontist to remotely monitor orthodontic braces on patients and make adjustments when necessary in a precise and predictable manner. In some implementations of the remote orthodontic system, the orthodontic system includes smart brackets in which each bracket has a miniature motor that drives a miniature gear, which in turn drives small rods or posts that push against an arch wire, generating a reaction force that pushes against the bracket's wings, in which the reaction force is transferred to the corresponding tooth to provide the required force for alignment of the tooth. The number of miniature motors and the configuration of the motor(s) can vary depending on design and functions. For example, the orthodontic system can include smart brackets in which each bracket has two miniature motors that drive miniature gears, which in turn pull or push an arch wire to generate opposing forces for alignment of the corresponding tooth (by generating couple forces system). In other implementations of the remote orthodontic system, the orthodontic system includes smart brackets in which each bracket has one or more miniature motors that drive one or more miniature gears, which in turn drive a rotatable base to provide root torque to the bracket for generating a force for alignment of the corresponding tooth. In some implementations of the remote orthodontic system, the orthodontic braces include arch wire segments connected by smart brackets in which each bracket has one or more miniature motors that apply forces to the arch wire segments, such that the combination of the forces generated by the plurality of brackets provide the proper amount of force for the alignment of each individual tooth.

Figure 1:
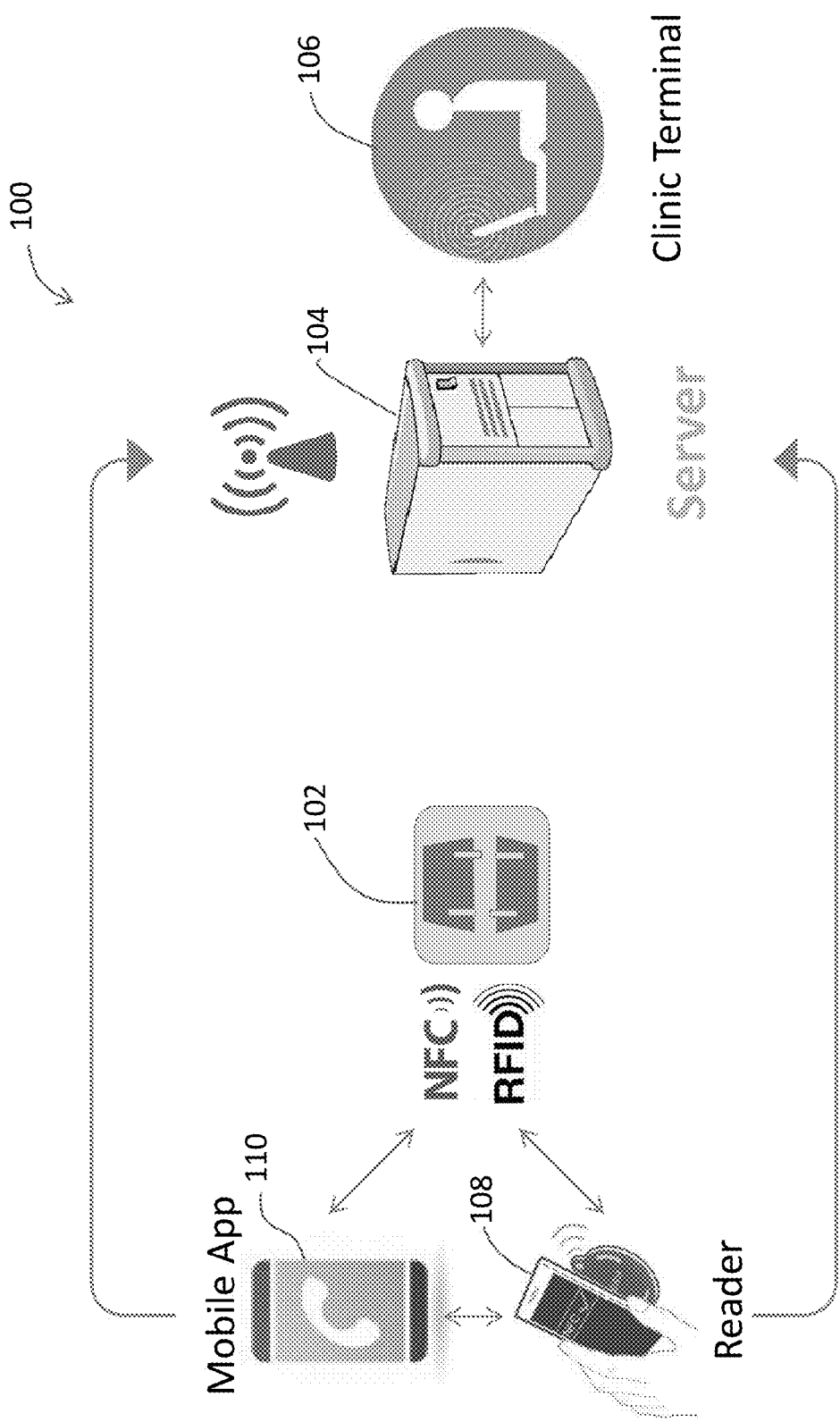
FIG. 1 is a diagram of an exemplary remote orthodontic system.

Referring to FIG. 1, a remote orthodontic system 100 includes orthodontic braces composed of smart brackets 102 (only one is shown in the figure) that communicate wirelessly with a computer server 104. The computer server 104 can be a physical machine located at the patient's home, or it can be a virtual server commonly referred to as a cloud server that resides remotely. The following describes examples in which the computer server 104 is a cloud server. In some examples, the computer server 104 may interact wirelessly with the brackets 102 by receiving signals from or sending signals to the brackets 102. This interaction occurs through, e.g., a home-based reader 108 or a user's cell phone 110, while the computer server 104 communicates with a clinic terminal 106 at a dental clinic. The computer server 104 receives signals from the brackets 102 (e.g., through the reader 108 or the cell phone 110), determines the current configurations of the brackets 102, determines whether adjustments are necessary, and sends back signals using the same route (e.g., through the reader 108 or the cell phone 110) to the brackets 102 in order to control motors in the brackets 102 to make the necessary adjustments. The computer server 104 communicates with the terminal 106 at the dental clinic to enable an orthodontist and/or other healthcare providers to monitor the configurations of the brackets 102 and enter commands to make additional adjustments when necessary.

In some implementations, when the patient first visits the orthodontist, the orthodontist may prescribe a treatment plan that specifies the amount and direction of force to be applied to each tooth at different time periods. The orthodontist may provide an electronic file that includes the treatment plan, and the patient may download, from the computer server 104, the electronic file having updated data containing the treatment plan to the reader 108 or the cell phone 110. The reader 108 or the cell phone 100 may execute an orthodontic application program that uses the information about the treatment plan to interact with the brackets 102.

After the first visit to the orthodontist, and at each follow up visit every three or four weeks, the orthodontist executes the orthodontic treatment program on the server 104. The orthodontic treatment program may analyze signals received from the brackets 102 to determine the progress of teeth alignment. The program may compare the current progress with the prescribed treatment plan and determine which brackets need to be adjusted to increase or decrease the force applied and its direction to the corresponding tooth, or to adjust the torque applied by the bracket to the tooth. The program instructs the server 104 to send signals to the brackets 102 to configure the brackets 102 such that each tooth receives the proper amount of force metrics according to the prescribed treatment plan.

Because the adjustments to the brackets 102 can be conveniently performed at the patient's home, the treatment plan may have instructions for more frequent bracket adjustments at finer time intervals, such as twice every month. The patient has the option of making adjustments to the brackets at times that are convenient to the patient.

The wireless reader 108 can interact wirelessly with the brackets 102 using a communication protocol similar to, e.g., the RFID protocol, Bluetooth protocol, or other protocols. The wireless reader 108 may be connected to the computer server 104 through a wire connection or a wireless link. The mobile phone 110 executing the orthodontic application program may interact wirelessly with the brackets 102 using a communication protocol similar to, e.g., the near-field communication protocol, Bluetooth protocol, or other protocols. The system may operate in, e.g., the 401-406 MHz, 902-928 MHz, 2400-2483.5 MHz, and/or 5725-5850 MHz bands. The mobile phone 110 may communicate with the computer server 104 through a wireless link.

In some implementations, the smart bracket 102 has sensors that can detect the amount of force (and/or the position trajectories) being applied to the tooth through the arch wire. Alternatively the sensors can be attached to or embedded in the arch wire itself. The sensors provide feedback signals so that the orthodontic treatment program executing on the computer server 104 can determine that the correct amount of force and the direction of force are applied to each tooth to ensure its proper alignment and positioning. If, after configuring the brackets 102, the sensors determine that the force/direction applied to the tooth deviates from the prescribed amount by more than a threshold value, the program may generate an alert signal, indicating that the patient should contact the orthodontist. Alternatively, the program can readjust and apply the new biomechanical force specifications. Upon receiving an instruction from the patient, the computer server 104 may send the data from the sensor to the clinic terminal 106 so that the orthodontist may determine whether it is possible to reconfigure the brackets remotely, or to inform the patient that it is necessary to return to the dental clinic for further examination and adjustment.

Figure 2:
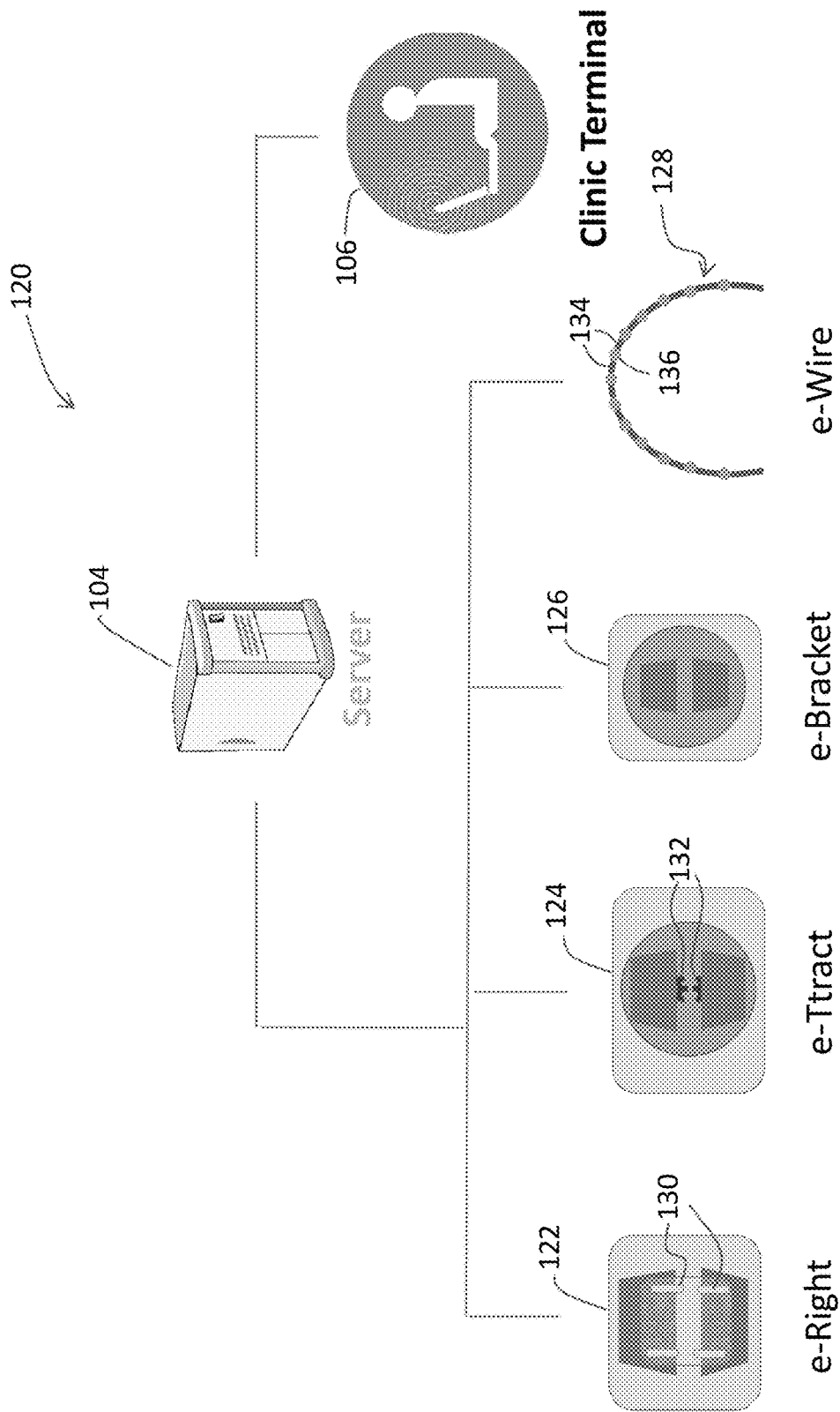
FIG. 2 is a diagram of various modules of the remote orthodontic system.

Referring to FIG. 2, a remote orthodontics system 120 may include a server 104 that communicates with different types of smart orthodontic braces, or orthodontic braces that include more than one type of smart brackets (individually or as a group). The computer server 104 may execute an orthodontic treatment program that is configured to control the various types of braces having various types of smart brackets. The server 104 may communicate with a clinic terminal 106 to enable an orthodontist to remotely monitor treatment progress or provide adjustments.

For example, one type of smart bracket is bracket 122, referred to as the e-Right bracket. The e-Right bracket 122 includes miniature motors that drive miniature gears, which in turn drive small rods 130 that push against an arch wire inserted into a slot of a bracket attached to a tooth. The small rods 130 provide forces that in combination produce the desired amount of force in the desired direction that is applied to the corresponding tooth to provide the required movement for alignment of the tooth.

A second type of smart bracket is bracket 124, referred to as the e-Tract bracket. The e-Tract bracket has two miniature motors that drive miniature gears 132, which in turn pull or push an arch wire (inserted in between) to generate retracting or protracting forces for movement and/or alignment of the corresponding tooth (or a group of teeth).

A third type of smart bracket is bracket 126, referred to as the e-Bracket in this document. The e-Bracket has one or more miniature motors that drive one or more miniature gears, which in turn drive a rotatable base to provide torque to the bracket 126 for generating a force for alignment of the corresponding tooth.

A fourth type of orthodontic braces variation is e-Wire braces 128. The e-Wire braces 128 include arch wire segments 134 connected to smart brackets 136 in which each bracket 136 has one or more miniature motors that apply forces to the arch wire segments 134, such that the interaction of the brackets 136 and wire segments 134 result in the proper amount of forces being applied to the teeth that need adjustment. Each arch wire segment is attached to the corresponding tooth surface in order to translate the delivered force. A patient may use any configuration of two or more of the e-Right bracket 122, e-Tract bracket 124, e-Bracket 126, or e-Wire braces 128 at the same time. The following describes details of the e-Bracket 126.

FIG. 3A shows a front view of an orthodontic bracket, referred to as an e-Bracket 220, and FIG. 3B shows a vertical mid-cross sectional view of the e-Bracket 220. The e-Bracket 220 is able to provide tooth alignment in all three-dimensions via a revolving base. The e-Bracket 220 includes a base 222 having a back surface 230 that is configured to be attached to a tooth, and a pivotable module 224 that can pivot relative to the base 222. The base 222 includes a front concave surface 232 that receives a back convex surface 234 of the pivotable module 224.

In some implementations, miniature motors and gear assemblies are configured to push an upper portion 240 of the pivotable module 224 forward or backward, and to push a lower portion 242 of the pivotable module 224 backward or forward, to cause the pivotable module 224 to pivot or rotate about a horizontal axis 236. This provides a torque that can be used for root movement.

Similarly, the miniature motors and gear assemblies are configured to push a left portion 244 of the pivotable module 224 forward or backward, and to push a right portion 246 of the pivotable module 224 backward or forward, to cause the pivotable module 224 to pivot or rotate about a vertical axis 238. This provides a force for correction of tooth alignment (in or out rotation movement).

In some implementations, the miniature motors and gear assemblies are configured to rotate the pivotable module 224 about an axis 254 in a clockwise or counterclockwise direction (as viewed from the front side). In this example, the axis 254 is along a horizontal lingual-facial direction. This provides a force to enable the action of tilting movement (also known as second order bend action).

In some examples, the e-Bracket 220 has a height L1 of about 6 mm and a length L2 of about 5 mm. The e-Bracket 220 can also have a square shape, with a side length of about 5 mm or 6 mm. The dimensions of the e-Bracket can vary depending on the size of the tooth being treated and the amount of force required.

Referring to FIG. 4, by operating the miniature motors and gear assemblies to push the left and/or right portions of the pivotable module 224, the pivotable module 224 can pivot or rotate about the vertical axis, as shown by the bi-directional arrow 250. By operating the miniature motors and gear assemblies to push the upper and/or lower portions of the pivotable module 224, the pivotable module 224 can pivot or rotate about the horizontal axis, as shown by the bi-directional arrow 252. This results in a multi-directional (three dimensional) integrated alignment system.

Referring to FIG. 5, the bracket 220 includes a miniature gear 260 that is supported by the base 222. The gear 260 engages notches in a rod 262 to drive the rod 262 forward or backward. The forward end of the rod 262 is coupled to the lower portion 242 of the pivotable module 224. When the rod 262 moves forward or backward, the rod 262 pushes the lower portion 242 forward or backward, respectively. Thus, by controlling the gear 260, the lower portion 242 can be moved forward or backward. In a similar manner, another gear (not shown in the figure) located at the upper portion of the base 222 drives a rod that in turn pushes the upper portion 240 of the pivotable module 224 forward or backward. Together these gears can cause the pivotable module 224 to pivot or rotate about the horizontal axis 236. The left portion 244 and the right portion 246 of the pivotable module 224 can be moved in a similar manner by two other gears and rods to cause the pivotable module 224 to pivot or rotate about the vertical axis 238.

In some implementations, bevel gears can be used to change the direction of rotation. For example, a miniature motor may drive a first conically shaped bevel gear that rotates about an axis that is parallel to the axis 254 (FIG. 3B), in which the first bevel gear drives a second conically shaped bevel gear that rotates about an axis parallel to the horizontal axis. The second bevel gear shares a same shaft as the gear 260. This allows the motor having an axis parallel to the axis 254 to be able to generate a force that drives the rod 262 forward or backward.

In some implementations, the gear 260 may be driven manually. For example, a lower rod 264 may have one end 266 that extends to outside of the base 222, in which the end 266 has one or more slots that can be driven by a small screwdriver. The rotation of the lower rod 264 drives the gear 260, which drives the upper rod 262 that in turn moves the lower portion 242 of the pivotable module 224.

In some implementations, the pivotable module 224 is connected to a node or ball 200 that fits in a track in the base 222. As the motor and gear assemblies push the upper, lower, left, and/or right potions of the pivotable module 224, the ball 200 moves inside the track while also anchoring the pivotable module 224.

Figure 6A:
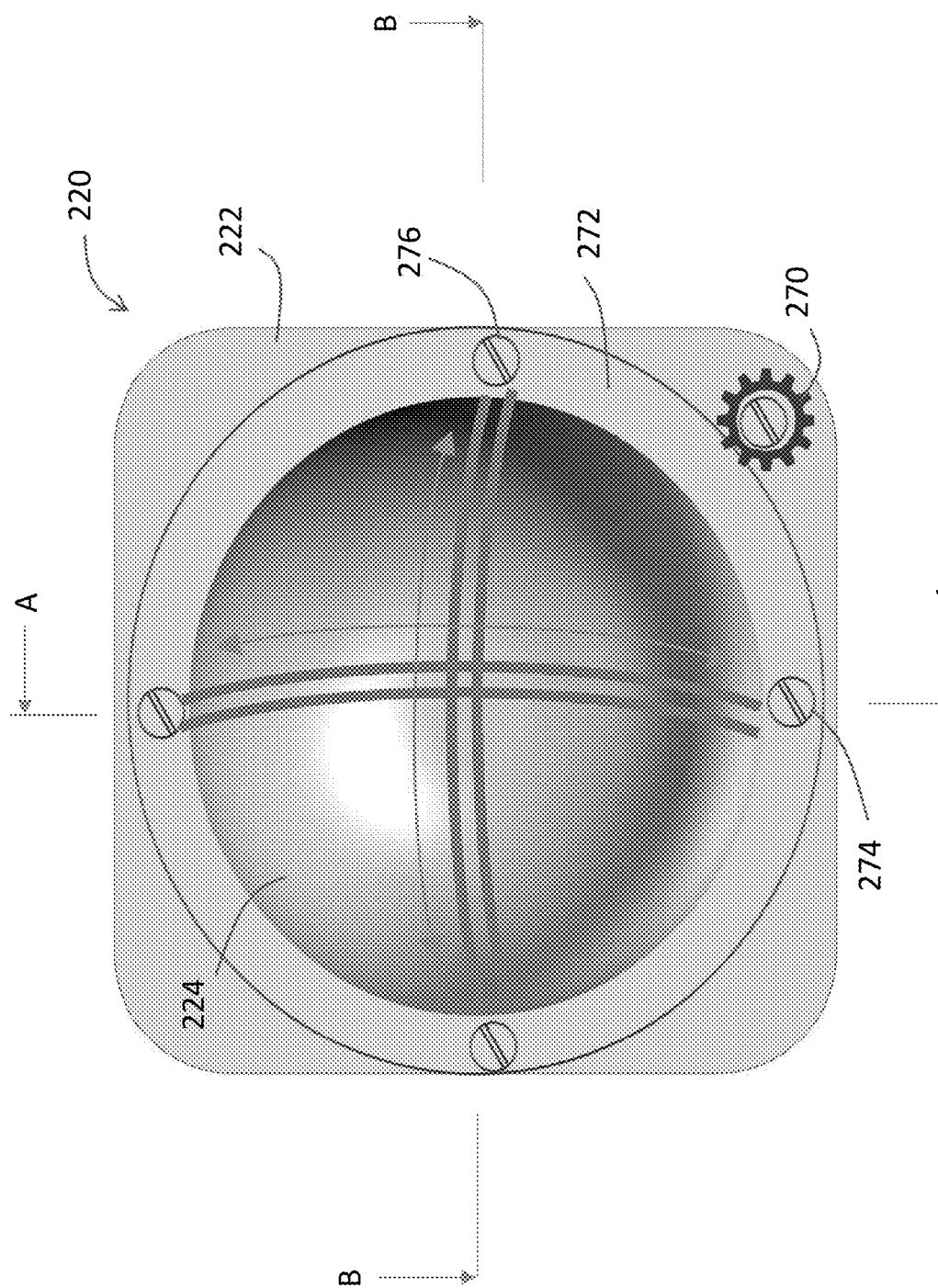
FIG. 6A is a diagram of an exemplary e-Bracket.

Referring to FIG. 6A, a fifth gear 270 can be configured to rotate the pivotable module 224 in a clockwise or counterclockwise direction (when viewed from a direction facing the front side of the bracket 220). The gear 270 can be configured to drive notches made in a circumference of the pivotable module 224, or to drive notches made in a flange 272 attached to the pivotable module 224.

In some implementations, screws 274 and 276 are provided for manually driving the gears of the orthodontic bracket 220. FIG. 6B shows across-sectional view of the orthodontic bracket 220 in the direction of the arrows on the line A-A of FIG. 6A. FIG. 6B is similar to FIG. 5 except that the screw 274 has been added. The lower rod 264 has an end that extends to outside of the base 222 and is coupled to the screw 274. When the user turns the screw 274, the lower rod 264 is rotated, which drives the gear 260, which drives the upper rod 262 that in turn moves the lower portion 242 of the pivotable module 224. This allows the pivotable module 224 to rotate about the horizontal axis 236.

FIG. 6C shows a cross-sectional view of the orthodontic bracket 220 in the direction of the arrows on the line B-B of FIG. 6A. The screw 276, rods 290 and 292, and a gear 294 are used to move the right portion 246 of the pivotable module 224. The rod 290 has an end that extends to outside of the base 222 and is coupled to the screw 276. When the user turns the screw 276, the rod 290 is rotated, which drives the gear 294, which drives the rod 292 that in turn moves the right portion 246 of the pivotable module 224. This allows the pivotable module 224 to rotate about the vertical axis 238.

In some implementations, additional screws, rods, and gears are used to enable the user to manually drive the left portion 244 and the upper portion 240, similar to driving the right portion 246 and the lower portion 242, respectively.

Figure 6D:
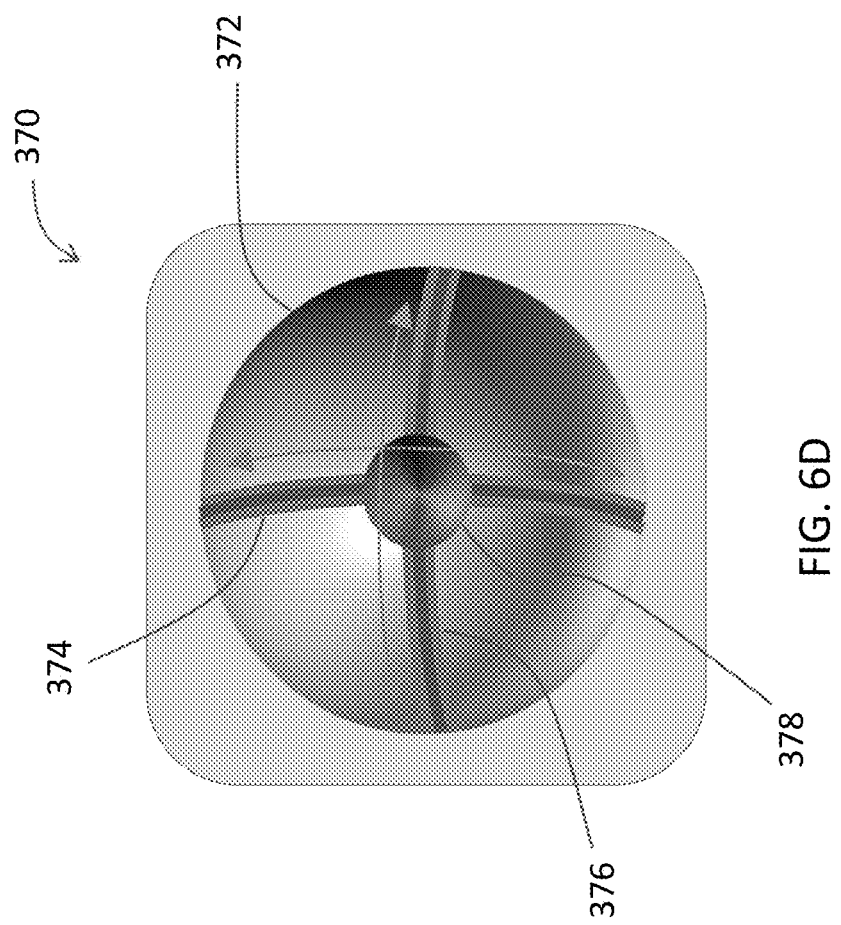
FIG. 6D is a diagram of a base of another exemplary e-Bracket.

Referring to FIG. 6D, in some implementations, an orthodontic bracket 370 similar to the e-Bracket 220 of FIGS. 3A and 3B can have a base 372 that has a vertical track 374 and a horizontal track 376. The node or ball 200 (connected to the pivotable module 224, FIG. 3B) can fit in the tracks 374 and 376. The base 372 includes a circular area 378 at the center of base to allow for free multi-directional force application before the node 200 enters the track 374 or 376. In this example, for the situations where the movements of the pivotable module 224 are small, the node 200 will remain in the circular area 378. The node 200 enters the track 374 or 376 when the movements of the pivotable module 224 are large.

Referring to FIGS. 3A, 3B, 7A, and 7B, a space 248 between the upper module 226 and the lower module 228 allows an arch wire 280 to pass through. When the pivotable module 224 pivots about the horizontal axis 236 or vertical axis 238, or rotates in a clockwise or counterclockwise direction, the upper module 226 and the lower module 228 exert force on the arch wire 280, and the reaction force from the arch wire 280 pushes back against the upper and lower modules 226, 228, generating a force that is applied to the tooth connected to the bracket 220. Depending on the pivotal or rotational movement of the pivotable module 224, the arch wire 280 can push back against the bracket in a variety of directions.

The bracket 220 may include an integrated circuit chip (e.g., shown in FIG. 8B). Each bracket can be assigned a unique identifier so that different brackets can be adjusted differently, enabling individual functionality to each of several e-Brackets mounted on the patient's teeth.

Referring to FIGS. 8A and 8B, in some implementations, the e-Bracket 220 can have a fixed or removable cover 260 that is used to ligate the arch wire 280 with the bracket slot. In some implementations, the base 222 includes an integrated circuit chip 282 that has circuitry for controlling the miniature motors that drive gear assemblies for pushing the upper portion 240 and lower portion 242 of the pivotable module 224. The integrated circuit chip 282 can communicate wirelessly to external devices, such as the reader 108 or the cell phone 110.

Figure 9:
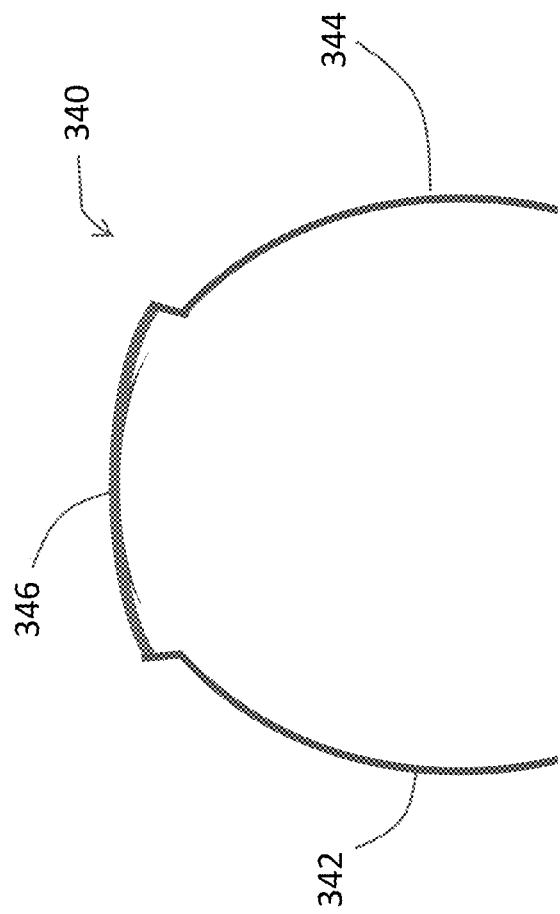
FIG. 9 is a diagram of a compensating arch wire.

Referring to FIG. 9, because the e-Bracket 220 (FIG. 3A) may be slightly thicker than conventional orthodontic brackets, it is useful to have a compensating arch wire 340 in which a portion 346 of the arch wire is offset from the rest of the arch wire. For example, the distance between the portion 346 of the arch wire to adjacent teeth is larger than the distance between a portion 342 or 344 of the arch wire to adjacent teeth. In some examples, the portion 346 of the arch wire coupled to smart brackets can be made of a material that is different from the other portions of the arch wire that are coupled to conventional brackets. In the example of FIG. 9, the e-Brackets are used for anterior teeth.

Various smart orthodontic brackets and wires have been described above. These smart brackets and wires can be used in the remote orthodontic system 100 of FIG. 1. Referring to FIG. 10, in order to monitor the movement of the tooth under treatment, markers can be attached to one or more adjacent teeth. For example, a smart bracket 350 is attached to a tooth 352 that needs to be aligned. A first marker 354 is attached to a tooth 356, and a second marker 358 is attached to another tooth 360. When the smart bracket 350 is first installed on the tooth 352, a set of one or more pictures of the teeth are taken. After a period of time, such as three or four weeks later, a second set of one or more pictures of the teeth are taken. The movement of the tooth 352 under treatment relative to the other teeth 356 and 360 can be measured by comparing the position of the bracket 350 relative to the markers 354 and 358 that function as reference points.

In some examples, the patient takes images of the teeth and sends them to the orthodontist, who monitors the progress of the treatment. If the movement of the tooth 352 is according to plan, then the smart bracket 350 will be adjusted according to plan. If the movement of the tooth 352 is outside of acceptable boundaries, then the orthodontist may adjust the treatment plan or ask the patient to return to the clinic for further examination and/or treatment. When the orthodontist needs to adjust the treatment plan, the orthodontist may send an instruction from the clinic terminal 106 to the server computer 104 to adjust the treatment plan stored locally at the server 104.

In some examples, the mobile phone 110 may execute an orthodontic app that provides instructions to the patient or a helper of the patient on how to take pictures in order to accurately determine the movement of the tooth 352. For example, a helper may use the camera on the mobile phone 110 to take pictures of the patient's teeth. A reference image that was previously taken can be overlaid on a live view taken by the phone camera. The reference image may show the two markers 354 and 358, so that the helper may position and orient the camera to take a picture of the teeth in which the markers 354 and 358 are at similar positions in the new picture. This makes it easier to compare the current picture with a previously taken picture to determine the movement of the tooth 352. A set of orthodontic biomechanical algorithms can be used by the system 100 to determine the auto adjustments to be made to the smart brackets, such as increasing or decreasing the forces applied by the gears in the e-Brackets.

The smart brackets may have sensors for sensing the force applied to the corresponding tooth. For example, a microelectromechanical sensor system having piezoresistive microsensors attached between the smart bracket and the tooth can be used to take measurements that can be used to calculate forces applied to the tooth in the x, y, and z directions, and moments in the x, y, and z directions. By monitoring the forces actually applied to the tooth, the system 100 can determine whether the gears in the smart brackets need to be adjusted to apply more or less force in a certain direction.

The chip 282 (FIG. 8B), the miniature motors, and the sensors system can be powered wirelessly by beaming power to microcoils in the smart brackets. The chip 282 may include circuitry for modulating data sent to the reader 108 or the server 104, or demodulating the signals sent from the reader 108 or the server 104.

The remote orthodontic system 100 helps orthodontists and their patients to have a high quality orthodontic treatment, with reduced visits to the dental office and reduced costs. For example, the adjustments to the smart brackets and arch wires can be made while the patients are at home. The orthodontists can also monitor the treatments and make adjustments to the treatment plans from home, allowing more flexible work schedules.

A novel orthodontic bracket that can generate and deliver forces has been described above. The system 100 is interactive in which the patient and the treatment provider are able to monitor the status of teeth alignment and report responses and symptoms. The system can be remotely controlled, enabling quick re-adjustment and auto-correction. The system can apply biomechanical equations based on the known static and dynamic equilibrium laws and algorithms. The system provides treatments with predictable and improved outcomes, so the treatment duration can be accurately forecasted and better controlled.

Each of the computer server 104, mobile phone 110, and reader 108 can include one or more processors and one or more computer-readable mediums (e.g., RAM, ROM, SDRAM, hard disk, optical disk, and flash memory). The one or more processors can perform various calculations or control functions described above. The calculations and various functions can also be implemented using application-specific integrated circuits (ASICs). The term "computer-readable medium" refers to a medium that participates in providing instructions to a processor for execution, including without limitation, non-volatile media (e.g., optical or magnetic disks), and volatile media (e.g., DRAM) and transmission media. Transmission media includes, without limitation, coaxial cables, copper wire and fiber optics.

The features described above can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language (e.g., C, Java), including compiled or interpreted languages, and it can be deployed in any form, including as a stand-alone program or as a module, component, subroutine, a browser-based web application, or other unit suitable for use in a computing environment.

Suitable processors for the execution of a program of instructions include, e.g., both general and special purpose microprocessors, digital signal processors, and the sole processor or one of multiple processors or cores, of any kind of computer. Generally, a processor will receive instructions and data from a read-only memory (ROM) or a random access memory (RAM) or both. The essential elements of a computer are a processor for executing instructions and one or more memories for storing instructions and data. Generally, a computer will also include, or be operatively coupled to communicate with, one or more mass storage devices for storing data files. The mass storage devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM, CD-R, DVD-ROM, DVD-R, Blu-ray DVD disks. The processor and the memory can be supplemented by, or incorporated in, ASICs (application-specific integrated circuits). The chip 282 (FIG. 8B) may include one or more processors described above. The chip 282 may also include one or more volatile or non-volatile memories for storing instructions to be executed by the one or more processors.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

Other embodiments are within the scope of the following claims. For example, a combination of various types of smart brackets can be used for treating one patient. The smart brackets and arch wires can be made of materials different from those described above. In some implementations, each bracket can include a radio frequency identification tag associated with a unique identifier. In some implementations, each chip (e.g., 272) has a unique identifier. This way, if a patient has multiple brackets, the server 104 can uniquely identify each bracket and send different instructions to different brackets.

What is claimed is:

1. An orthodontic bracket, comprising:
   a base configured to be attached to a surface of a tooth; and
   a rotatable module having a first member and a second member, the rotatable module being rotatably coupled to the base, the first and second members being spaced apart to define an archwire slot configured to receive an archwire,
   wherein the base comprises a miniature gear system to drive the rotatable module relative to the base, in which the miniature gear system comprises a first gear and a first rod, the first rod has a first portion that engages the first gear and a second portion that extends to a first portion of the rotatable module, and when the first gear rotates in a specified direction, the first gear drives the first rod to apply a first force to the first portion of the rotatable module to cause the rotatable module to rotate relative to the base,
   wherein the miniature gear system comprises a second gear and a second rod, the second rod has a first portion that engages the second gear and a second portion that extends to a second portion of the rotatable module, and when the second gear rotates in a specified direction, the second gear drives the second rod to apply a second force to the second portion of the rotatable module to cause the rotatable module to rotate relative to the base, and
   wherein when the first gear drives the first rod to push the first portion of the rotatable module, the second gear drives the second rod to move away from the second portion of the rotatable module.

2. The orthodontic bracket of claim 1 in which the first gear drives the first rod to apply the first force to the first portion of the rotatable module to cause the rotatable module to rotate about an axis along a distal-mesial direction.

3. The orthodontic bracket of claim 1 in which the first gear drives the first rod to apply the first force to the first portion of the rotatable module to cause the rotatable module to rotate about an axis along an occlusal-gingival direction.

4. The orthodontic bracket of claim 1 in which the first gear is configured to be driven manually.

5. The orthodontic bracket of claim 1, further comprising a cover attached to the first and second members to retain the archwire within the archwire slot.

6. The orthodontic bracket of claim 1 in which the miniature gear system further comprises a third gear that engages the rotatable module to rotate the rotatable module about an axis along a lingual-facial direction.

7. The orthodontic bracket of claim 1 in which the base comprises a concave surface, the rotatable module comprises a convex surface that is complementary of the concave surface of the base, and the convex surface of the rotatable module faces the concave surface of the base.

8. The orthodontic bracket of claim 1, comprising a first miniature motor to drive the miniature gear system.

9. The orthodontic bracket of claim 8, comprising a wireless energy transfer module to receive energy wirelessly for powering the first miniature motor.

10. The orthodontic bracket of claim 8, comprising an integrated circuit having circuitry to control the first miniature motor.

11. The orthodontic bracket of claim 10 in which the integrated circuit comprises a communication module to communicate wirelessly with an external device.

12. The orthodontic bracket of claim 11 in which the integrated circuit is configured to receive instructions wirelessly and control the first miniature motor according to the instructions.

13. The orthodontic bracket of claim 1, comprising a sensor to detect a force applied by the bracket to the tooth.

14. The orthodontic bracket of claim 13, comprising a wireless energy transfer module to receive energy wirelessly for powering the sensor.

15. A system comprising the orthodontic bracket of claim 13 and the archwire.

16. The orthodontic bracket of claim 1, comprising a radio frequency identification tag associated with a unique identifier.

17. The orthodontic bracket of claim 1,
   wherein the base has a first track and the rotatable module is rotatably coupled to the base through a node that fits in the first track, and
   the node slides along the first track as the rotatable module rotates relative to the base.

18. The orthodontic bracket of claim 17 in which the base has a second track, the first track extending along a horizontal direction and the second track extending along a vertical direction when the orthodontic bracket is attached to the surface of the tooth.

19. The orthodontic bracket of claim 1,
   wherein the rotatable module has an ellipsoid shape and has a first dimension parallel to the archwire slot that is greater than a second dimension along a front-rear direction, a rear of the rotatable module facing the base.

20. A method comprising:
   attaching a base of an orthodontic bracket to a surface of a tooth, the orthodontic bracket having a base and a rotatable module rotatably coupled to the base, the rotatable module having a first member and a second member, the first and second members being spaced apart to define an archwire slot,
   inserting an archwire into the archwire slot;
   rotating the rotatable module relative to the base, including:
      rotating a first gear in a specified direction to drive a first rod that has a first portion that engages the first gear and a second portion that extends to a first portion of the rotatable module, and causing the first rod to apply a first force to the first portion of the rotatable module to cause the rotatable module to rotate relative to the base, and
      rotating a second gear in a specified direction to drive a second gear and a second rod that has a first portion that engages the second gear and a second portion that extends to a second portion of the rotatable module, and causing the second rod to apply a second force to the second portion of the rotatable module to cause the rotatable module to rotate relative to the base;
   in response to the rotations of the first and second gears in the specified directions, generating a force based on an interaction of the archwire and walls of the archwire slot and transmitting the force to the tooth;
   wherein when the first gear drives the first rod to push the first portion of the rotatable module, the second gear drives the second rod to move away from the second portion of the rotatable module.

21. The method of claim 20 in which using the first gear to drive the first rod to push the first portion of the rotatable module comprises pushing at least one of an occlusal portion, a gingival portion, a mesial portion, or a distal portion of the rotatable module to cause the rotatable module to rotate relative to the base.

22. The method of claim 20 in which rotating the rotatable module comprises rotating the rotatable module about an axis along a distal-mesial direction.

23. The method of claim 20 in which rotating the rotatable module comprises rotating the rotatable module about an axis along an occlusal-gingival direction.

24. The method of claim 20, comprising driving a gear system to rotate the rotatable module, in which the gear system comprises the first gear and the second gear.

25. The method of claim 24, comprising manually drive the gear system.

26. The method of claim 24, comprising using a miniature motor to drive the gear system.

27. The method of claim 26, comprising transmitting energy wirelessly to a wireless energy transfer module to power the miniature motor.

28. The method of claim 26, comprising operating an integrated circuit to control the miniature motor.

29. The method of claim 28, comprising operating the integrated circuit to communicate wirelessly with an external device.

30. The method of claim 29, comprising, at the integrated circuit, receiving instructions wirelessly from the external device and controlling the miniature motor according to the instructions.

31. The method of claim 20, further comprising attaching a cover to the first and second members to retain the archwire within the archwire slot.

32. The method of claim 20, comprising using a sensor to sense a force applied by the bracket to the tooth.

33. The method of claim 32, comprising transmitting energy wirelessly to a wireless energy transfer module to power the sensor.

34. The method of claim 20, comprising probing a radio frequency identification tag attached to the bracket to identify a unique identifier associated with the tag.

35. An orthodontic bracket, comprising:
a base configured to be attached to a surface of a tooth;
a rotatable module having an occlusal member and a gingival member, the rotatable module being rotatably coupled to the base, the occlusal member and the gingival member being spaced apart to define an archwire slot between the occlusal member and the gingival member, the archwire slot configured to receive an archwire,
wherein the base comprises a miniature gear system to drive the rotatable module relative to the base, in which the miniature gear system comprises a first gear and a first rod, the first rod has a first portion that engages the first gear and a second portion that extends to a first portion of the rotatable module, and when the first gear rotates in a specified direction, the first gear drives the first rod to apply a first force to the first portion of the rotatable module to cause the rotatable module to rotate relative to the base;
wherein the miniature gear system comprises a second gear and a second rod, the second rod has a first portion that engages the second gear and a second portion that extends to a second portion of the rotatable module, and when the second gear rotates in a specified direction, the second gear drives the second rod to apply a second force to the second portion of the rotatable module to cause the rotatable module to rotate relative to the base, and
wherein when the first gear drives the first rod to push the first portion of the rotatable module, the second gear drives the second rod to move away from the second portion of the rotatable module.

36. The orthodontic bracket of claim 35 in which the first gear drives the first rod to apply the first force to the first portion of the rotatable module to cause the rotatable module to rotate about an axis along a distal-mesial direction.

37. The orthodontic bracket of claim 35 in which the first gear drives the first rod to apply the first force to the first portion of the rotatable module to cause the rotatable module to rotate about an axis along an occlusal-gingival direction.

38. The orthodontic bracket of claim 35 in which the first gear is configured to be driven manually.

39. The orthodontic bracket of claim 35, further comprising a cover attached to the occlusal and gingival members to retain the archwire within the archwire slot.

40. The orthodontic bracket of claim 35 in which the at least one of the first and second gears engages the rotatable module to rotate the rotatable module about an axis along a lingual-facial direction.

41. The orthodontic bracket of claim 35 in which the base comprises a concave surface, the rotatable module comprises a convex surface that is complementary of the concave surface of the base, and the convex surface of the rotatable module faces the concave surface of the base.

42. The orthodontic bracket of claim 35, comprising a first miniature motor to drive the miniature gear system.

43. The orthodontic bracket of claim 42, comprising a wireless energy transfer module to receive energy wirelessly for powering the first miniature motor.

44. The orthodontic bracket of claim 42, comprising an integrated circuit having circuitry to control the first miniature motor.

45. The orthodontic bracket of claim 44 in which the integrated circuit comprises a communication module to communicate wirelessly with an external device.

46. The orthodontic bracket of claim 45 in which the integrated circuit is configured to receive instructions wirelessly and control the first miniature motor according to the instructions.

47. The orthodontic bracket of claim 35, comprising a sensor to detect a force applied by the bracket to the tooth.

48. The orthodontic bracket of claim 47, comprising a wireless energy transfer module to receive energy wirelessly for powering the sensor.

49. The orthodontic bracket of claim 35, comprising a radio frequency identification tag associated with a unique identifier.

50. A method comprising:
attaching a base of an orthodontic bracket to a surface of a tooth, the orthodontic bracket having a base and a rotatable module rotatably coupled to the base, the rotatable module having an occlusal member and a gingival member, the occlusal member and the gingival member being spaced apart to define an archwire slot between a gingival surface of the occlusal member and an occlusal surface of the gingival member,
inserting an archwire into the archwire slot;
rotating the rotatable module relative to the base, including:
rotating a first gear in a specified direction to drive a first rod that has a first portion that engages the first gear and a second portion that extends to a first portion of the rotatable module, and causing the first rod to apply a first force to the first portion of the rotatable module to cause the rotatable module to rotate relative to the base, and rotating a second gear in a specified direction to drive a second rod that has a first portion that engages the second gear and a second portion that extends to a second portion of the rotatable module, and causing the second rod to apply a second force to the second portion of the rotatable module to cause the rotatable module to rotate relative to the base;

in response to the rotations of the first and second gears in the specified directions, generating a force based on an interaction of the archwire and walls of the archwire slot and transmitting the force to the tooth;

wherein when the first gear drives the first rod to push the first portion of the rotatable module, the second gear drives the second rod to move away from the second portion of the rotatable module.

51. The method of claim 50, in which using the first gear to drive the first rod to push the first portion of the rotatable module comprises pushing at least one of an occlusal portion, a gingival portion, a mesial portion, or a distal portion of the rotatable module to cause the rotatable module to rotate relative to the base.

52. The method of claim 50 in which causing the rotatable module to rotate relative to the base comprises rotating the rotatable module about an axis along a distal-mesial direction.

53. The method of claim 50 in which causing the rotatable module to rotate relative to the base comprises rotating the rotatable module about an axis along an occlusal-gingival direction.

54. The method of claim 50, comprising driving a gear system to rotate the rotatable module, in which the gear system comprises the first gear and the second gear.

55. The method of claim 54, comprising manually drive the gear system.

56. The method of claim 54, comprising using a miniature motor to drive the gear system.

57. The method of claim 56, comprising transmitting energy wirelessly to a wireless energy transfer module to power the miniature motor.

58. The method of claim 56, comprising operating an integrated circuit to control the miniature motor.

59. The method of claim 58, comprising operating the integrated circuit to communicate wirelessly with an external device.

60. The method of claim 59, comprising, at the integrated circuit, receiving instructions wirelessly from the external device and controlling the miniature motor according to the instructions.

61. The method of claim 50, further comprising attaching a cover to the occlusal and gingival members to retain the archwire within the archwire slot.

62. The method of claim 50, comprising using a sensor to sense a force applied by the bracket to the tooth.

63. The method of claim 62, comprising transmitting energy wirelessly to a wireless energy transfer module to power the sensor.

64. The method of claim 50, comprising probing a radio frequency identification tag attached to the bracket to identify a unique identifier associated with the tag.

65. An orthodontic bracket, comprising:

a base configured to be attached to a surface of a tooth; and a rotatable module having a first member and a second member, the rotatable module being rotatably coupled to the base, the first and second members being spaced apart to define an archwire slot configured to receive an archwire, wherein the base comprises a miniature gear system to drive the rotatable module relative to the base, in which the gear system comprises a first gear and a first rod, the first rod has a first portion that engages the first gear and a second portion that extends to a first portion of the rotatable module, and when the first gear rotates in a specified direction, the first gear drives the first rod to apply a first force to the first portion of the rotatable module to cause the rotatable module to rotate relative to the base;

a first screw that is configured to be manually driven; and a second rod that is configured to be driven by the first screw, in which the second rod is configured to drive the first gear to cause the first gear to drive the first rod to apply the first force to the first portion of the rotatable module to cause the rotatable module to rotate relative to the base along a first direction.

66. The orthodontic bracket of claim 65, comprising:

a second screw that is configured to be manually driven, and a third rod that is configured to be driven by the second screw, in which the third rod is configured to drive a second gear to cause the second gear to drive a fourth rod to apply a second force to a second portion of the rotatable module to cause the rotatable module to rotate relative to the base along a second direction that is different from the first direction.

* * * * *

UNITED STATES PATENT AND TRADEMARK OFFICE
CERTIFICATE OF CORRECTION

PATENT NO. : 10,159,541 B2  
APPLICATION NO. : 15/160291  
DATED : December 25, 2018  
INVENTOR(S) : Naif Bindayel Page 1 of 1

It is certified that error appears in the above-identified patent and that said Letters Patent is hereby corrected as shown below:

In the Claims

Column 12  
Line 50, in Claim 20, delete "a second gear and a second rod" and insert -- a second rod --.

Signed and Sealed this  
Second Day of April, 2019

Andrei Iancu  
*Director of the United States Patent and Trademark Office*